United States Patent
Hoang et al.

(10) Patent No.: US 8,476,056 B2
(45) Date of Patent: Jul. 2, 2013

(54) **THERMOTOLERANT *ACTINOMADURA* STRAIN CAPABLE OF DEGRADING POLYESTERS**

(75) Inventors: Kim-Chi Hoang, Taipei (TW); Shu-Feng Yang, Taipei (TW); Min Tseng, Hsinchu (TW); Gwo-Fang Yuan, Hsinchu (TW)

(73) Assignee: Food Industry Research and Development Institute, Taiwan (CN)

( * ) Notice: Subject to any disclaimer, the term of this patent is extended or adjusted under 35 U.S.C. 154(b) by 261 days.

(21) Appl. No.: 12/858,492

(22) Filed: Aug. 18, 2010

(65) Prior Publication Data

US 2012/0171743 A1 Jul. 5, 2012

Related U.S. Application Data

(63) Continuation-in-part of application No. 11/977,402, filed on Oct. 24, 2007, now abandoned.

(51) Int. Cl.
*C12N 1/12* (2006.01)

(52) U.S. Cl.
USPC .................... 435/252.1; 435/170; 435/243

(58) Field of Classification Search
None
See application file for complete search history.

(56) References Cited

PUBLICATIONS

Lipski et al., International Journal of Systematic Bacteriology, 1995, vol. 45, No. 4, p. 717-723.*
Listing of claims filed on Oct. 24, 2007 in the Parent U.S. Appl. No. 11/977,402.*
Shimao, M. "Biodegradation of Plastics," *Current Opinion in Biotechnology*, vol. 12, (2001) pp. 242-247.
Takeda, M. et al. "Thermostable Poly(3-hydroxybutyrate) Depolymerase of a Thermophilic Strain of *Leptothrix* sp. Isolated from a Hot Spring," *J. Ferment. Bioeng.* vol. 85, No. 4, (1998) pp. 375-380.
Tansengco, M.L., et al. "Thermophilic Microbial Degradation of Polythylene Succinate," *World J. Microbiol. Biotechnol.* vol. 14, (1998) pp. 133-138.
Sanchez, J., et al. "Degradation of Polycaprolactone at 50°C by a Thermotolerant *Aspergillus* sp." *Biotechnol. Lett.* vol. 22, (2000) pp. 849-853.
Kleeberg, I., et al. "Biodegradation of Aliphatic-Aromatic Copolyesters by *Thermomonospora fusca* and Other Thermophilic Compost Isolates" *Appl. Environ. Microbiol.* vol. 64. No. 5, (1998) pp. 1731-1735.
Jarerat, A., et al. "Degradation of Poly(tetramethylene succinate) by Thermophilic Actinomycetes" *Biotechnol. Lett.* vol. 23, (2001) pp. 647-651.
Calabia, B., et al. "Microbial Degradation of Poly(D-3-hydroxybutyrate) by New Thermophilic Streptomyces Isolates" *Biotechnol. Lett.* vol. 26, (2004) pp. 15-19.
Tokiwa et al., Macromol, Symp. 2003, vol. 201, p. 283-289.
Sasaki et al., The Journal of Antibiotics, 1988, vol. XLI, No. 7, p. 835-842.
Zhang et al., International Journal of Systematic and Evolutionary Microbiology, 2001, vol. 51, p. 373-383.
M. Tseng, et al, *Actinomadura* . . . actinomycete, International Journal of Systematic and Evolutionary Microbiology, 2009, vol. 59, p. 517-520.
Chinese Office Action With Search Report Issued on May 31, 2011, and English Translation of Search Report.
Yutaka Tokowa et al., Microbial degradation of aliphatic polyesters, vol. 201, Issue 1, pp. 283-289, Obtober 2003 pp. 285-288, Figure 2.
Sasaki T et al., New antibiotics SF2315A and B produced by an *Excellospora* sp. I. Taxonomy of the strain, isolation and characterization of antibiotics. J Antibiot (Tokyo). Jul. 1988,41(7):835-842 p. 837, Table 2.
G. N. Chen et al., Studies on the degrading capability of thermophillic acitnomycetes (BC445-5) to polyethylene succinate (PES) (translated by Lee and Li), 2007 Annual Polymer Conference, Conference date: Jan. 19, 2007-Jan. 20, 2007 Whole document.
ID: D86943/from NCBI databases,Sep. 6, 2007 Whole document.
Amnat Jarerat and Yutaka Tokiwa, Degradation of poly(tetramethylene succinate) by thermophilic actinomycetes. vol. 23, No. 8, 647-651. Whole document, 2001.

* cited by examiner

*Primary Examiner* — Kade Ariani
(74) *Attorney, Agent, or Firm* — Ladas & Parry LLP (57) ABSTRACT

A new thermotolerant *Actinomadura* sp., which is capable of degrading polyesters, is provided. Compositions comprising the species for use in degrading polyesters are also provided. The invention also relates to methods for degrading polyesters by using the strain and the composition.

19 Claims, 3 Drawing Sheets

THERMOTOLERANT *ACTINOMADURA* STRAIN CAPABLE OF DEGRADING POLYESTERS

CROSS-REFERENCE TO RELATED APPLICATION

This application is a continuation-in-part of application Ser. No. 11/977,402 filed on Oct. 24, 2007 now abandoned, claims the benefit thereof and incorporates the same by reference.

FIELD OF THE INVENTION

The present invention relates to a novel thermotolerant *Actinomadura* species, which is capable of degrading polyesters, and the use thereof. The present invention also provides a method of degrading polyesters.

BACKGROUND OF THE INVENTION

Poly (D-3-hydroxybutyrate) (PHB) is a natural biodegradable and biocompatible polyester that can be synthesized by many microorganisms and accumulated therein as carbon and energy reserve. Because PHB can be completely degraded by many microorganisms in the environment without forming any toxic products, it can be used to make biodegradable plastics (Shimao 2001). Several studies have described the isolation and characterization of aerobic and anaerobic microorganisms that can degrade PHB. Most of these studies were carried out at ambient temperatures (25° C.-30° C.) but little data is available on the microbial degradation of PHB at a higher range of temperature.

However, thermophilic composting is one of the most promising technologies in recycling biodegradable plastics, and thermophilic/thermotolerant microorganisms play an important role in the composting process. Most studies on high-temperature polyester degradation were focused on bacteria and fungi (Takeda et al., 1998; Tansengco & Tokiwa, 1998; Sanchez et al., 2000). There is still a need for thermophilic/thermotolerant microorganisms that are able to degrade polyesters under high temperature conditions.

Actinomycetes are antibiotic-producing microorganisms. There is a vast amount of reports on actinomycetes enzyme-production and degradation abilities in vitro. Actinomycetes are usually considered to be the most active microorganism in the later stages of decomposition of plant and other materials, and play an important role in polyester degradation. Some thermophilic/thermotolerant actinomycetes that can degrade polyesters have been reported. Kleeberg et al. (1998) disclose the degradation of terephthalic acid (BTA) by *Thermobifida fusca* (former name: *Thermomonosproa fusca*). Jarerat & Tokiwa (2001) disclose the degradation of poly(tetramethylene succinate) (PTMS) by *Microbispora rosea* subsp. *aerata* IFO 14046, *Microbispora rosea* subsp. *aerata* IFO 14047, *Actinomadura* sp. (former name: *Excellospora japonica*) IFO 14486, and *A. viridilutea* (former name: *E. viridilutea*) JCM 339. *M. rosea* subsp. *aerata* IFO 14046 also could degrade poly(ε-caprolactone)(PCL), PHB and poly(lactide)(PLA). Calabia & Tokiwa (2004) disclose the degradation of PHB, poly(ethylene succinate) (PES), poly(ester cargonate) (PEC), PCL, and poly(butylenes succinate) (PBS) by *Streptomyces* sp. strain MG. However, no thermophilic/thermotolerant PHB degradation in genus *Actinomadura* has been reported. We surprisingly found that a thermotolerant *Actinomadura* strain isolated from the environment has polyester degrading ability at a high temperature environment.

SUMMARY OF THE INVENTION

One purpose of the present invention is to provide an isolated *Actinomadura* sp. capable of degrading polyesters. Preferably, the isolated *Actinomadura* is strain BC44T-5 or the variant or mutant thereof, and the polyester is PHB.

Another purpose of the present invention is to provide a composition comprising the isolated *Actinomadura* sp. of the invention. The composition may be used in combination with one or more other microorganisms. It would be preferable if said one or more other microorganisms are capable of degrading polyesters.

A further purpose of the present invention is to provide a method for degrading polyesters comprising the step of contacting the polyesters with the isolated *Actinomadura* sp. of the invention or with the composition of the invention.

Still another purpose of the present invention is to provide a method for degrading polyesters comprising the step of contacting polyesters with a microorganism selected from the group consisting of *Actinomadura nitritigenes*, *Actinomadura rubrobrunea*, *Actinomadura rugatobispora*, and a combination thereof.

The present invention is described in detail in the following sections. Other characterizations, purposes and advantages of the present invention can be easily found in the detailed descriptions and claims of the invention.

DETAILED DESCRIPTION OF THE INVENTION

Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. The nomenclatures used in connection with, and the laboratory procedures and techniques of, analytical chemistry, synthetic organic chemistry, and medicinal and pharmaceutical chemistry described herein are those well known and commonly used in the art.

As utilized in accordance with the present disclosure, the following terms, unless otherwise indicated, shall be understood to have the following meanings:

The term "isolated" or "isolation" means that the material is removed from its original environment (e.g., the natural environment if it is naturally existing). The term "isolated" does not necessarily reflect the extent to which the microorganism has been purified. In contrast, a "substantially pure culture" of the strain of microorganism refers to a culture which contains substantially no other microorganisms than the desired strain or strains of microorganism. In other words, a substantially pure culture of a strain of microorganism is substantially free of other contaminants, which can include microbial contaminants as well as undesirable chemical contaminants. The conventional isolation method includes serial dilution method.

The term "thermotolerant" or "thermophilic" refers to a growth characteristic of an organism which thrives at relatively high temperatures, such as at above 45° C., preferably about 45° C. to 50° C., most preferably at about 50° C.

The standard concept of definition of "species" for the purpose of taxonomy of bacteria is based on DNA-DNA relatedness. A bacterium is considered to represent a novel species in a genus when DNA-DNA hybridization rate of the bacterium to the most related species in the genus is less than 70%. The DNA-DNA hybridization rate is determined on the basis of the method disclosed in Ezaki et al. (1989).

The term "mutant" or "variant" is meant to encompass any microorganism whose total cellular genetic composition has been altered, for example, by chemical mutagenesis, spontaneous mutation, genetic engineering, transformation, or transfection, such that its physical or biochemical properties are affected. However, its ability to degrade polyester is not detrimentally affected.

The term "actinobacteria" or "actinomycetes" refers to a group of Gram-positive bacteria. Most are found in the soil, and they include some of the most common soil life, playing an important role in decomposition of organic materials, such as cellulose and chitin. This replenishes the supply of nutrients in the soil and is an important part of humus formation. Other actinobacteria inhabit plants and animals, including a few pathogens, such as *Mycobacterium*. Some actinobacteria form braching filaments, which somewhat resemble the mycelia of the unrelated fungi, among which they were originally classified under the older name actinomycetes. Most members are aerobic, but a few, such as *Actinomyces israelii*, can grow under anaerobic conditions. Unlike the Firmicutes, the other main group of Gram-positive bacteria, they have DNA with a high GC-content and some actinomycetes species produce external spores.

The genus "*Actinomadura*," belonging to class Actinobacteria, was firstly described by Lechevalier and Lechevalier in 1970 and currently comprises more than 30 validly published species. Members of the genus are aerobic, Gram-positive, no-acid-fast, non-motile organisms. Non-fragmentary substrate mycelia are present and aerial hyphae differentiate into spore chains. The spore chains are of various lengths and can be straight, hooked or spiral on the tips of the aerial mycelium. Spores are oval or short rod-like with smooth or warty surface and non-motile. The organism contains meso-diaminopimelic acid ($A_2$pm), madurose, glucose, and galactose are detected in whole-cell sugars (type B). Major cellular fatty acids are iso-$C_{16:0}$, $C_{16:0}$, $C_{17:0}$, and 10-methyl-$C_{17:0}$. Phosphatidylethanolamine is present as a diagnostic phospholipid. The major menaquinones are MK-9($H_4$) and MK-9($H_6$). Mycolic acids are absent. Members of the genus have a DNA G+C content of about 65-69 mol %. The *Actinomadura* sp. of the present invention not only refers to bacterial cultures in solution or on growth plates but also to precipitates and pellets of bacteria obtainable from the *Actinomadura* sp. comprising media or solutions. It further refers to dried, freeze dried, frozen (−180° C. or −70° C.) or cooled cultures of the bacteria of the present invention.

The term "degradability" relates to the maximal percentage of a substrate that can be degraded in a degradation process under conditions as described in the example section. The degradability of the *Actinomadura* sp. of the present invention is more than 50%, preferably more than 80%, more preferably more than 90%, or even more preferably more than 95%.

The term "polyester" or "polyesters" refers to a category of polymers which contain an ester functional group in their main chain. Examples of polyester include, but are not limited to polyethylene terephthalate (PET), PTMS, PCL, PHB, PLA, PES, PEC and PBS.

The term "composition" in the present invention refers to both liquid as well as solid media. Examples of such liquid and solid media are bacterial growth media and buffered solutions.

Unless otherwise required by context, singular terms shall include pluralities and plural terms shall include the singular. *Actinomadura* sp.

One object of the invention is to provide a substantially pure species of *Actinomadura* genus which comprises: short spores chain on the tips of aerial mycelium; non-motile and rod spores with a spiny surface; blue aerial spore mass; an absence of soluble pigment production; an ability to grow at about 25° C. to 55° C.; an ability to hydrolyse casein, aesculin and L-tyrosine; an ability to produce nitrate reductase; an ability utilize glucose, xylose, rhamnose, sorbitol, fructose, trehalose and lactose; and a DNA-DNA hybridization rate with *Actinomadura miaoliensis* BC44T-5 of at least 70%. In a preferred embodiment of the invention, the DNA-DNA hybridization rate is at least 75%, 80%, 90%, or 95%.

According to the present invention, the novel species of the present invention are capable of degrading polyesters, preferably PHB, at a high temperature, such as at least about 45° C., preferably at about 45° C. to about 50° C., and most preferably at about 50° C.

A preferred strain of the present invention is BC44T-5, which is found to have 100% polyester degradability at about 50° C.

Sequence comparison of the almost completed 16S rDNA sequence of BC44T-5 revealed that its closest relatives in the phylogenetic tree are *A. viridilutea* and *A. rubrobrunea*. According to the DNA-DNA hybridization results, the strain BC44T-5 and these two species belong to separate species.

The BC44T-5 strain is a gram-positive, aerobic, non-acid fast, and thermotolerant organism. Short spore chains are borne on the tips of the aerial mycelia, and the spores are rod with a spiny surface, and non-motile. No soluble pigment is produced. Growth occurs between about 25° C. and about 55° C. The hydrolysis of casein, aesculin and L-tyrosine and the production of nitrate reductase are positive. The utilization of glucose, xylose, rhamnose, sorbitol, fructose, trehalose, and lactose is observed, while that of inositol, arabinose, galactose and inulin is not. The utilization of mannitol, raffinose, salicin, sucrose and maltose is doubtable. The cell-wall peptidoglycan contains meso-$A_2$pm. Madurose, arabinose, glucose, rhamnose and ribose are detected in the whole-cell hydrolysates. Predominant menaquinones are MK-9($H_4$) and MK-9($H_2$). Mycolic acids are not detected. The diagnostic phospholipid is phosphatidylethanolamine (PE). The major cellular fatty acids are iso-$C_{16:0}$ (14.8%), C16:0 (14.6%), C17:0 (13.8%) and 10-methyl$C_{17:0}$ (23.8%). The G+C content of the DNA is 70.6%.

On the basis of the polyphasic taxonomic characteristics, the phenotypic properties, the phylogenetic and the genetic data, it is proposed that the strain BC44T-5 should be classified as a novel species of the genus *Actinomadura*, named *Actinomadura miaoliensis* sp. nov (M. Tseng et al., 2009).

Composition

Another object of the invention is to provide a composition comprising the isolate of the invention for use in degrading polyesters. The composition may contain suitable growth media, carriers, diluents, inert materials, or other additives.

The composition can be used in combination with one or more other microorganisms that do not detrimentally affect the activity of the isolate. Preferably, the one or more microorganisms are polyester-degrading microorganisms, such as *Thermobifida fusca*, *Microbispora rosea* subsp. *aerata*, *Actinomadura* sp., *A. viridilutea*, *Aspergillus* sp. strain ST-01, *Thermoascus aurantiacus*, *Leptothrix* sp., *Actinomadura nitritigenes*, *Actinomadura rubrobrunea*, *Actinomadura rugatobispora*, and *Actinomadura viridilutea*.

Another object of the invention is to provide a composition comprising a microorganism selected from the group consisting of *Actinomadura nitritigenes*, *Actinomadura rubrobrunea*, *Actinomadura rugatobispora*, and a combination thereof. Preferably, the microorganism is selected from the group consisting of *Actinomadura nitritigenes* BCRC 16816, *Actinomadura rubrobrunea* BCRC 16817, *Actinomadura rugatobispora* BCRC 13608 and a combination thereof. The composition can also be used in combination with one or more other polyester-degrading microorganisms, such as *Thermobifida fusca*, *Microbispora rosea* subsp. *aerata*, *Actinomadura* sp., *A. viridilutea*, *Aspergillus* sp. strain ST-01, and *Thermoascus aurantiacus*, *Leptothrix* sp.

Utility

A further object of the invention is to provide a method for degrading polyesters comprising the step of contacting the polyesters with the isolated *Actinomadura* sp. of the invention, *Actinomadura nitritigenes*, *Actinomadura rubrobrunea*, *Actinomadura rugatobispora*, or a combination thereof, or with the compositions of the invention. The above-mentioned microorganisms can be *Actinomadura miaoliensis* BC44T-5, *Actinomadura nitritigenes* BCRC 16816, *Actinomadura rubrobrunea* BCRC 16817 and/or *Actinomadura rugatobispora* BCRC 13608. According to the invention, the contact can be made in the presence of one or more other polyester-degrading microorganisms, such as *Thermobifida fusca*, *Microbispora rosea* subsp. *aerata*, *Actinomadura* sp., *A. viridilutea*, *Aspergillus* sp. strain ST-01, and *Thermoascus aurantiacus*, *Leptothrix* sp.

As a result, the invention can decompose and degrade polyesters without environmental pollution, and the products having low molecular weights can be returned into a substance-recycling system in the natural environment.

The method of the invention can be applied to a container, a wrapping material, as well as a fiber and cloth, each of them is made of polyesters. When the wastes containing polyesters are subjected to composts, the *Actinomadura* sp. of the invention can rapidly decompose the polyesters to nontoxic substances. Alternatively, when the wastes containing polyesters are reclaimed, the *Actinomadura* sp. can be added into the wastes to degrade the polyesters.

The following examples are provided to aid those skilled in the art in practicing the present invention. Even so, the examples should not be construed to unduly limit the present invention as modifications and variations in the embodiments discussed herein may be made by those having ordinary skill in the art without departing from the spirit or scope of the present inventive discovery.

EXAMPLES

Isolation of Actinomycete Strains

Actinomycetes strains were isolated from a soil sample collect from Miaoli county, Taiwan, by using HV agar (see Hayakawa & Nonomura, 1987), and incubated at 50° C. for 7 days. The strains were maintained on oatmeal agar (Difco) and stored at −20° C. as suspension of spores or mycelia fragments in glycerol (20%, vol/vol).

Preparation of Emulsified PHB/Agar Plates

One gram of PHB powder was dissolved in 50 ml of methylene chloride. The solution was emulsified into basal medium containing (per liter): yeast extract, 0.1 g; $FeSO_4.7H_2O$, 10 mg; $MgSO_4.7H_2O$, 0.2 g; $(NH_4)_2SO_4$, 1 g; $CaCl_2.2H_2O$, 20 mg; NaCl, 0.1 g; $Na_2MoO_4.2H_2O$, 0.5 mg; $NaWO_4.2H_2O$, 0.5 mg; $MnSO_4.H_2O$, 0.6 mg; and detergent (Poas, Nice Co., Taiwan), 50 mg. Methylene chloride was evaporated by using a proctor laboratory hood. Agar (18 g) was added to the emulsified medium with a pH of 7.2. The medium was then sterilized in an autoclave at 121° C. for 15 minutes and poured into Petri dishes.

Polyester-Degrading Screening

Clear-zone method was used to screen the polyester degradation of isolates. The purified isolates of actinomycetes were streaked on emulsified PHB/agar plates, and incubated at 50° C. for 7 days. The degradation ability of the isolates was determined by the formation of a clear zone around the colonies.

Figure 1:
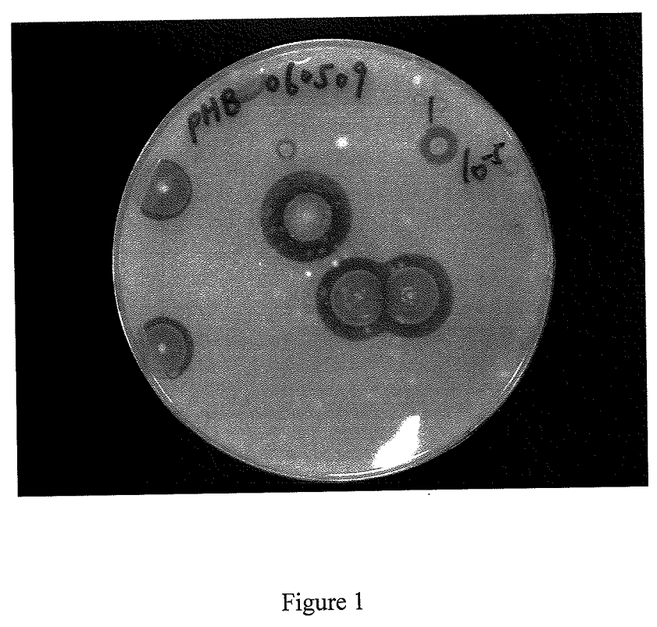
FIG. 1 shows clear zones formed around the colonies of strain BC44T-5 on a PHB/agar plate in polyester-degrading screening.

During the screening of the polyester-degradating actinoycetes, several thermophilic strains were identified. One isolate having the highest degradability on polyester was identified and named BC44T-5. The results of polyester-degrading screening of BC44T-5 were shown in FIG. 1.

Deposit of Microorganism

The isolated strain BC44T-5 was deposited with the American Type Culture Collection, (ATCC, 10801 University Boulevard, Manassas, Va. 20110-2209, USA) in accordance with the Budapest Treaty on 3 May 2007, and assigned the accession No. PTA-8409.

Characterization of Strain BC44T-5

(1) Morphological Characteristics

The strain BC44T-5 was incubated on oatmeal agar for 7 days at 50° C. After incubation, the culture was fixed by 4% osmium tetraoxide solution, and then dehydrated by serial ethanol, acetone and critical point drying. The morphological characteristics of the strain BC44T-5 were observed by scanning electron microscope (S-3000N, Hitachi, Tokyo).

Figure 2:
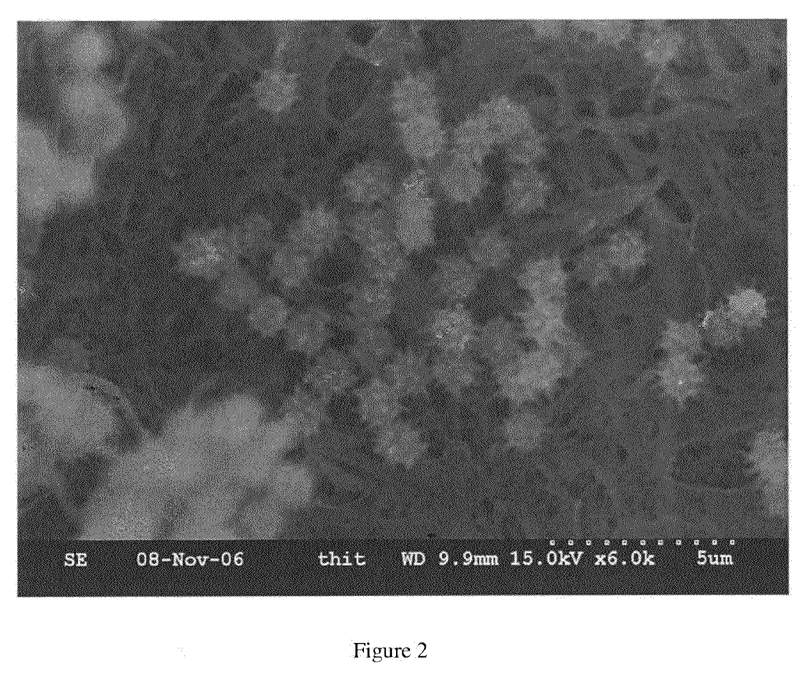
FIG. 2 shows a scanning electron micrograph of the strain BC44T-5, which was grown on oatmeal agar at 50° C. for 7 days.

The micrograph of the strain BC44T-5 grown on oatmeal agar was shown in FIG. 2. It was found that the strain BC44T-5 produces branched and non-fragmented substrate mycelia, and short spore chains are borne on the aerial mycelia. The spores are non-motile, rod and spiny. The aerial spore mass is blue.

(2) Physiological and Biochemical Characteristics

Physiological tests were performed at 50° C. Growth temperature, hydrolysis of aesculin, casein, hypoxanthine, xanthine, adenine, L-tyrosine, production of amylase, nitrate reductase, urease and melanin were detected by the method disclosed in Gordon et al. (1974). Sole carbon source utilization tests were conducted by the method disclosed in Shirling & Gottlieb (1966).

There is no soluble pigment produced by the strain in all of the media tested. The results of the physiological and biochemical tests are presented in Table 1.

TABLE 1

The Physiological Characteristics of the Strain BC44T-5

| Characteristics | Reaction |
| --- | --- |
| Growth temperature (° C.) | 25-55 |
| Decomposition of: | |
| Adenine | − |
| Aesculin | + |
| Casein | + |
| Hypoxanthine | − |
| L-tyrosine | + |
| Xanthine | − |
| Production of: | |
| Amylase | − |
| Melanin | − |
| Nitrate reductase | + |
| Urease | − |
| Growth on sole carbon source of: | |
| Glucose | + |
| Xylose | + |
| Inositol | − |
| Mannitol | +/− |
| Rhamnose | + |
| Raffinose | +/− |
| Salicin | +/− |
| Sorbitol | + |
| Fructose | + |
| Sucrose | +/− |
| Arabinose | − |
| Galactose | − |
| Trehalose | + |
| Inulin | − |
| Maltose | +/− |
| Lactose | + |

*+: positive reaction, −: negative reaction, +/−: doubtful reaction (3) Cellular Biochemical Characteristics Biomass for the chemotaxonomic studies was prepared following a growth in shaking flasks (125 rpm/min) of YG broth (10.0 g of yeast extract and 10.0 g of glucose in 1.0 L of distilled water, pH 7.0) at 50° C. for 7 days. The isomer of diaminopimelic acid and sugars in whole-cell hydrolysates were determined by the method disclosed in Hasegawa et al. (1983). The presence of mycolic acids was examined via TLC following the method disclosed in Minnikin et al. (1975), and phospholipids were extracted and identified following the method disclosed in Minnikin et al. (1984). Menaquinones were extracted and purified by the method disclosed in Collins et al. (1977) and then analyzed by HPLC (Model 600, Waters) with a Nova-Pak C18 column. For quantitative analysis of the cellular fatty acid content, the strain BC44T-5 was cultivated in TSB medium at 50° C. on a shaking incubator at 125 rpm for 7 days. The extracts of the methylated fatty acids were prepared according to the protocol provided by the manufacturer (Microbial ID, Inc. U.S.A.)

The results show that the strain BC44T-5 contains meso-$A_2$pm, madurose, glucose and galactose in the whole-cell hydrolysates. Predominant menaquinones found are MK-9 ($H_4$), MK-9($H_2$); and mycolic acids were not detected. Phosphatidylethanolamine (PE) was detected. The major fatty acid methyl esters are Iso-$C_{16:0}$ (14.82%), $C_{16:0}$ (14.63%), $C_{17:0}$ (13.79%), and 10-methyl$C_{17:0}$ (23.77%). The G+C content of the DNA is 70.6 mol %.

(4) Phylogentic Characteristics

For extracting the DNA to be used for sequencing the 16S rDNA, the strain BC44T-5 was cultivated in YG broth at 50° C. for 7 days. Cells were removed from the broth using a pipette tip and the total DNA was extracted by using QIAGEN® Genimic DNA Kit. The G+C content of the DNA was determined by the HPLC method disclosed in Tamaoka & Komagata (1984). The DNA sample was prepared using the same method described above. The 16S rDNA was PCR-amplified using the methods disclosed in Nakajima et al (1999) and then directly sequenced on an automatic DNA sequencer (ABI model 3730) by using BigDye Terminator V3.1 Kit (Applied Biosystems).

The almost-complete 16S rDNA sequence (1514 nt) of the strain BC44T-5 was determined as follows:

(SEQ ID NO: 1)

```
1
TAGAGTTTGA TCCTGGCTCA GGACGAACGC TGGCGGCGTG CTTAACACAT GCAAGTCGAG CGGAAAGGCC CCTTCGGGGG

100
TACTCGAGCG GCGAACGGGT

101
GAGTAACACG TGAGCAACCT GCCCCTGACT CTGGGATAAG CCTGGGAAAC CGGGTCTAAT ACCGGATACG ACCTCCGTNG

200
GCATCCNTTG GTGGTGGAAA

201
GTTTTTCGGT TGGGGATGGG CTCGCGGCCT ATCAGCTTGT TGGTGGGGTG ATGGCCTACC AAGGCGACGA CGGGTAACCG

300
GCCTGAGAGG GCGACCGGTC

301
ACACTGGGAC TGAGACACGG CCCAGACTCC TACGGGAGGC AGCAGTGGGG AATATTGCGC AATGGGCGGA AGCCTGACGC

400
AGCGACGCCG CGTGGGGGAT
```

```
401
GACGGCCTTC GGGTTGTAAA CCTCTTTCAG CAGGGACGAA GCTTTCGGGT GACGGTACCT GCAGAAGAAG CGCCGGCTAA
                500
CTACGTGCCA GCAGCCGCGG

501
TAATACGTAG GGCGCAAGCG TTGTCCGGAA TTATTGGGCG TAAAGAGCTC GTAGGTGGTT TGTCGCGTCG GATGTGAAAG
                600
CCCATGGCTT AACTGTGGGT

601
CTGCATTCGA TACGGGCAGA CTAGAGGTAG GTAGGGAGC ATGGAATTCC CGGTGTAGCG GTGAAATGCG CAGATATCGG
                700
GAGGAACACC GGTGGCGAAG

701
GCGGTGCTCT GGGCCTTACC TGACGCTGAG GAGCGAAAGC GTGGGAGCG AACAGGATTA GATACCCTGG TAGTCCACGC
                800
CGTAAACGTT GGGCGCTAGG

801
TGTGGGGTTC TTCCACGGAT TCCGCGCCGT AGCTAACGCA TTAAGCGCCC CGCCTGGGGA GTACGGCCGC AAGGCTAAAA
                900
CTCAAAGGAA TTGACGGGGG

901
CCCGCACAAG CGGCGGAGCA TGTTGCTTAA TTCGACGCAA CGCGAAGAAC CTTACCAAGG CTTGACATCA CCCGAAAACT
                1000
CGCAGAGATG CGGGGTCCTT

1001
TTTGGGCGGG TGACAGGTGG TGCATGGCTG TCGTCAGCTC GTGTCGTGAG ATGTTGGGTT AAGTCCCGCA CACGAGCGCA
                1100
ACCTCGTTCC ATGTTGCCAG

1101
CACGTAGTGG TGGGGACTCA TGGGAGACCG CCGGGGTCAA CTCGGAGGAA GGTGGGGATG ACGTCAAGTC ATCATGCCCC
                1200
TTATGTCTTG GGCTGCAAAC

1201
ATGCTACAAT GGCCGGTACA GAGGGCTGCG ATACCGTGAG GTGGAGCGAA TCCCTTAAAG CCGGTCTCAG TTCGGATTGG
                1300
GGTCTGCAAC TCGACCCCAT

1301
GAAGTCGGAG TCGCTAGTAA TCGCAGATCA GCAACGCTGC GGTGAATACG TTCCCGGGCC TTGTACACAC CGCCCGTCAC
                1400
GTCACGAAAG TCGGCAACAC

1401
CCGAAGCCCG TGGCCCAACC CTTTGGGGGG GAGCGGTCGA AGGTGGGGCC GGCGATTGGG ACGAAGTCGT AACAAGGTAG
                1500
CCGTACCGGA AGGTGCGGCT 1501        1514
GGATCACCTC CTTA
```

Preliminary comparison of the sequence against the GenBank database revealed high sequence similarity values with members of the genus *Actinomadura*.

Multiple sequence alignments of the 16S rDNA sequence of the strain BC44T-5 and other valid published *Actinomadura* species and other related species were preformed using the software CLUSTAL_X (see Thompson et al., 1997). Phylogenetic analysis was performed using the software packages PHYLIP (see Felsenstein, 1993) and MEGA (Molecular Evolutionary Genetics Analysis) version 2.1 (see Kumar et al., 2001) after multiple alignments. Evolutionary distances were calculated (distance options according to the Kimura two-parameter model; see Kimura, 1980, 1983) and the sequences were clustered with the neighbor-joining method (see Saitou & Nei, 1987). Bootstrap analysis with 1000 resamplings (see Felsenstein, 1985) was performed to evaluate the tree topology of the neighbor joining data.

Figure 3:
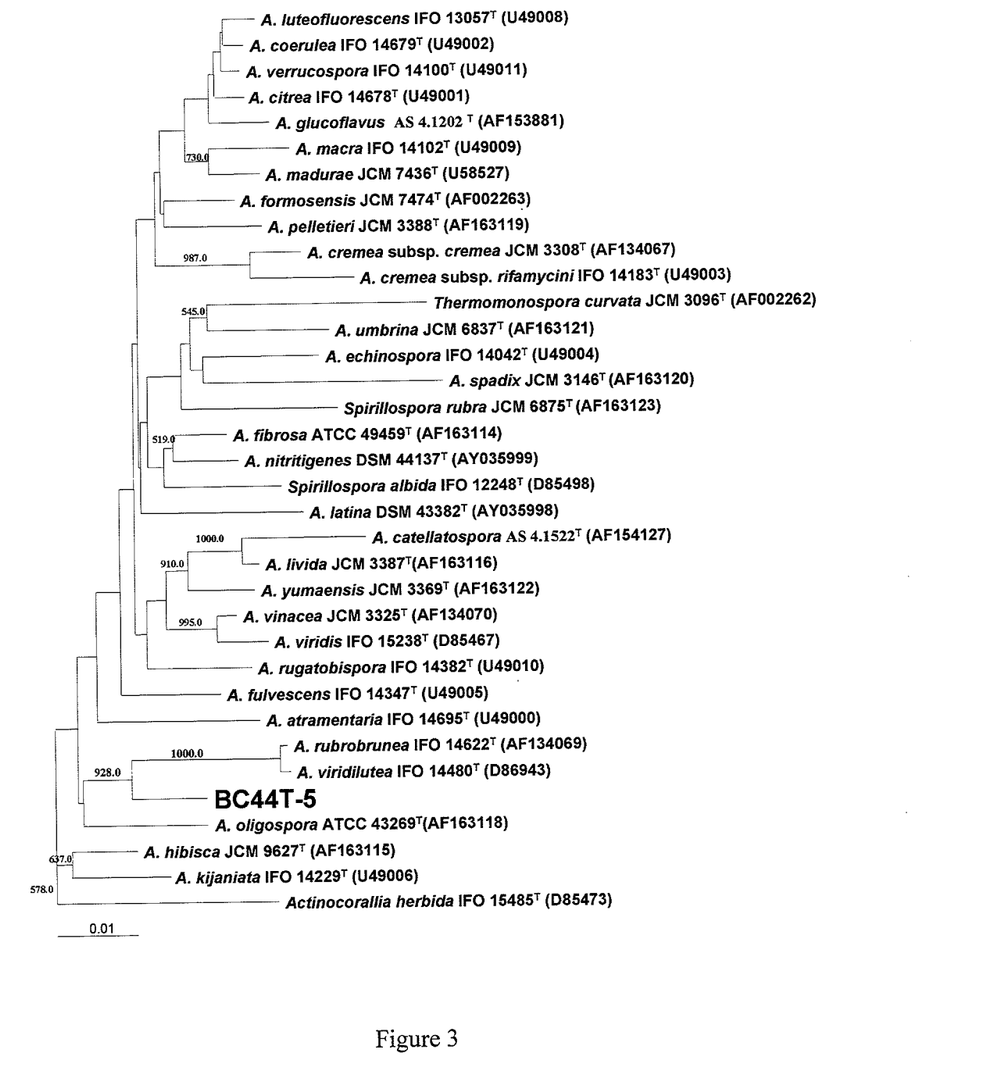
FIG. 3 shows a neighbour-joining tree (Saitou & Nei, 1987) based on the almost complete 16S rDNA sequences. The neighbour joining tree shows the phylogenetic position of strain BC44T-5 within the *Actinomadura* species. Numbers at nodes indicate percentage of 1000 bootstrap resamplings and only values over 50% are given. The scale bar represents 0.01 substitutions per nucleotide position.

The phylogenetic tree based on the 16S rDNA sequences of the strain BC44T-5 and the other valid published *Actinomadura* species and other related species is shown in FIG. 3. Binary similarity values ranged between 96.5% (*A. vividilute*[T] BCRC 13638) and 98.2% (*A. rubrobrunea*[T] BCRC 16817) (NCBI).

DNA-DNA Hybridization

DNA-DNA hybridization was carried out based on the method disclosed in Ezaki et al. (1989). DNA-DNA hybridization rates of the strain BC44T-5 to its closest type strains of *A. viridilutea*[T] (BCRC 13638) and *A. rubrobrunea*[T] (BCRC 16817) are 50.1% and 53.2% (shown in Table 2).

TABLE 2

DNA Hybridization Rate Among Specise of *Actinomadura*

| Probe | BC44T-5 (%) | *A. viridilutea*[T] (%) | *A. rubrobrunea*[T] (%) |
| --- | --- | --- | --- |
| BC 44T-5[T] | 100.0 | 47.6 | 27.8 |
| *A. viridilutea*[T] | 50.1 | 100.0 | 69.6 |
| *A. rubrobrunea*[T] | 53.2 | 64.7 | 100.0 |

It is clear from the DNA-DNA relatedness (<70%) study that the strain BC44T-5 and the two strains, *A. viridilutea*[T] (BCRC 13638) and *A. rubrobrunea*[T] (BCRC 16817), belong to different species (see Wayne et al., 1987).

The distinctiveness of the strain BC44T-5 also comes from the phenotypic evidence compared with the nearest phylogenetic neighbours shown in FIG. 2. Based on the phenotypic and genotypic characteristics, the strain BC44T-5 should be classified as a new species of the genus *Actinomadura*. The strain BC44T-5 is named *Actinomadura miaoliensis* sp. nov., with the type strain BC44T-5.

Polyester Degradability (1) Polyester Degradability at Different Temperatures

The polyester degradation abilities of the isolated strain BC44T-5 at different temperatures were tested by the clear-zone methods. The actinomycetes of the purified isolates were streaked on emulsified PHB agar plates, and then the plates were incubated at 30, 37, 45, 50 and 55° C. for 7 days. Degradation abilities of the isolates were determined by measuring the diameter of the clear zone formed around the colonies. The results of the polyester degradation tests are presented in Table 3.

TABLE 3

Polyester Degradation of BC44T-5 at Different Temperature

| | Temperature (° C.) | | | | |
| --- | --- | --- | --- | --- | --- |
| | 30 | 37 | 45 | 50 | 55 |
| Reaction[a] | − | + | +++ | +++ | − |

[a]−: clear zone does not formed; +: clear zone is smaller than 1 mm; ++: clear zone is between 1 and 3 mm; +++: clear zone is larger than 3 mm As shown in Table 3, clear zones were observed on the PHB plates which were incubated at 37, 45 and 50° C. According to the size of clear zone, the optimal degradability can be obtained between 45 and 50° C.

(2) Polyester Degradability of Different Actinomycetes

The polyester degradation abilities of different *Actinomadura* strains were tested according to the methods described above. The optimal temperature for the incubation varied depending on the *Actinomadura* strain used. The results of the polyester degradation tests are presented in Table 4.

TABLE 4

Clear Zone Forming Ability of *Actinomadura* Strains

| Strain[b] | Optimal temperature (° C.) | Clarity of clear zone on plate containing with PHB[a] |
| --- | --- | --- |
| BC44T-5 | 50 | +++ |
| *Actinomadura citrea* BCRC 13352 | 28 | − |
| *Actinomadura cremea* subsp. *cremea* BCRC 13394 | 28 | − |
| *Actinomadura echinospora* BCRC 12547 | 28 | − |
| *Actinomadura formosensis* BCRC 16355 | 28 | − |
| *Actinomadura kijaniata* BCRC 13416 | 28 | − |
| *Actinomadura luteofluorescens* BCRC 16250 | 28 | − |
| *Actinomadura macra* BCRC 13378 | 28 | − |
| *Actinomadura nitritigenes* BCRC 16816 | 28 | +++ |
| *Actinomadura oligospora* BCRC 16818 | 28 | − |
| *Actinomadura rubrobrunea* BCRC 16817 | 55 | +++ |
| *Actinomadura rugatobispora* BCRC 13608 | 28 | +++ |
| *Actinomadura viridilutea* BCRC 13638 | 45 | +++ |
| *Actinomadura viridis* BCRC 13398 | 28 | − |
| *Actinomadura viridis* BCRC 13399 | 28 | − |
| *Actinomadura viridis* BCRC 13410 | 28 | − |

[a]Clear-zone forming adility: −, clear zone does not formed; +: clear zone is smaller than 1 mm; ++: clear zone is between 1 and 3 mm; +++: clear zone is larger than 3 mm.
[b]All strains shown in Table 4 are commercial available from the Bioresource Collection and Research Center (BCRC) of the Food Industry Research and Development Institute (FIRDI), 331 Shih-Pin Rd., Hsinchu, Taiwan, R.O.C.

As shown in Table 4, in addition to the isolated strain BC44T-5, four other strains, *Actinomadura nitritigenes* BCRC 16816, *Actinomadura rubrobrunea* BCRC 16817, *Actinomadura rugatobispora* BCRC 13608, and *Actinomadura viridilutea* BCRC 13638 are found to have the polyester degradation ability, and the strains *Actinomadura nitritigenes* BCRC 16816, *Actinomadura rubrobrunea* BCRC 16817, *Actinomadura rugatobispora* BCRC 13608 were never known to have such ability before the invention.

(3) Polyester Degradability at Different Incubation Period

The strain BC44T-5 was inoculated into a 250 ml Erlenmeyer flask containing 100 ml of basal medium and 100 mg of PHB film to analyze the biodegradability of the strain to PHB. The PHB film was prepared by the heat pressed method. The film having a thickness of about 188 μm to 220 μm was sterilized with 75% (wt./vol.) alcohol and radiated for 10 minutes. The flasks were incubated on a rotary shaker (180 rpm) at 50° C. The results are shown in Table 5.

TABLE 5

Polyester-degrading screening results of BC44T-5

| | Days | | | | | |
|---|---|---|---|---|---|---|
| | 0 | 2 | 4 | 6 | 8 | 10 |
| Color of culture solution | transparent | light brown | brown | dark brown | dark brown | dark brown |
| Weight of bacteria (mg) | — | 20.9 | 41.5 | 36.1 | 34.3 | 36.3 |
| Initial weight of PHB (mg) | — | 52 | 53.1 | 51.4 | 51.8 | 51.7 |
| The weight of PHB after degradation (mg) | — | 34.4 | 20.5 | 3.7 | 0 | 0 |
| The weight of degraded PHB(mg) | — | 17.6 | 32.6 | 47.7 | 51.8 | 51.7 |
| Degradability (%) | — | 33.8 | 61.4 | 92.8 | 100 | 100 |
| pH value | 7 | 7.41 | 7.42 | 7.36 | 7.05 | 7.26 |
| TOC | | 5653 | 6765 | 7255 | 9495 | 6520 |
| KHP ppm | | 4.647 | 5.641 | 6.078 | 8.079 | 5.422 |

The degradability test shows that the strain BC44T-5 can totally (100%) degrade the PHB film after an 8-day incubation in the liquid medium.

REFERENCES

Calabia, B. P. & Tokiwa, Y. (2004). Microbial degradation of poly(D-3-hydroxybutyrate) by a new thermophilic *Streptomyces* isolate. *Biotechnol. Lett.* 26, 15-19.

Collins, M. D., Pirouz, T., Goodfellow, M. & Minnikin, D. E. (1977). Distribution of menaquinones in actinomycetes and corynebacteria. *J Gen Microbiol* 100, 221-230.

Ezaki, T., Hashimoto, Y., & Yabuuchi, E. (1989). Fluorometric deoxyribonucleic acid-deoxyribonucleic acid hybridization in microdilution wells as an alternative to membrane filter hybridization in which radioisotopes are used to determine genetic relatedness among bacterial strains. *Int J Syst Bacteriol* 39, 224-229.

Felsenstein, J. (1985). Confidence limits on phylogenies: an approach using the bootstrap. *Evolution* 39, 783-791.

Felsenstein, J. (1993). PHYLIP (phylogeny inference package), version 3.5c. Department of Genetics, University of Washington, Seattle, USA.

Gordon, R. E., Barnett, D. A., Handerhan, J. E. & Pand, C. H.-N. (1974). *Nocardia coeliaca, Nocardia autotrophica,* and the nocardin strain. *Int J Syst Bacteriol* 24, 54-63.

Hasegawa, T., Takizawa, M. & Tanida, S. (1983). A rapid analysis for chemical grouping of aerobic actinomycetes. *J Gen Appl Microbiol* 29, 319-322.

Hayakawa, M. & Nonomura, H. (1987). Humic acid-vitamin agar, a new medium for the selective isolation of soil actinomycetes. *J Ferment Technol* 65, 501-509.

Jarerat, A., & Tokiwa, Y. (2001). Degradation of poly(tetramethylene succinate) by thermophilic actinomycetes. *Biotechnol. Lett.* 23, 647-651.

Kleeberg, L., Hetz, C., Kroppenstedt, R. M., Müller, R. J. & Deckwer, W.-D. (1998). Biodegradation of aliphatic-aromatic copolyesters by *Thermomonospora fusca* and other thermophilic compost isolates. *Appl. Environ. Microbiol.* 64, 1731-1735.

Kimura, M. (1980). A simple method for estimating evolutionary rates of base substitutions through comparative studies of nucleotide sequence. *J Mol Evol* 16, 111-120.

Kimura, M. (1983). The neutral theory of molecular evolution. Cambridge: Cambridge University Press.

Kumar, S., Tamura, K., Jakobsen, I. B. & Nei, M. (2001). MEGA2: Molecular Evolutionary Genetics Analysis software. *Bioinformatics* 17, 1244-1245.

Lechevalier, M. P. & Lechevalier, H. A. (1970). A critical evaluation of the genera of aerobic actinomycetes. In *The Actinomycetales*, pp. 393-405. Edited by H. Prauser. Jena: Gustav Fisher.

Minnikin, D. E., Alshamaony, L. & Goodfellow, M. (1975). Differentiation of *Mycobacterium, Nocardia,* and related taxa by thin layer chromatographic analysis of whole-cell methanolysates. *J Gen Microbiol* 88, 200-204.

Minnikin, D. E., O'Donnell, A. G., Goodfellow, M., Alderson, G., Athalye, M., Schall, A. & Parlett, J. H. (1984). An intergrated procedure for the extraction of isoprenoid quinines and polar lipids. *J. Microbiol. Methods* 2, 233-241.

M. Tseng, S.-F. Yang, K.-C. Hoang, H.-C. Liao, G.-F. Yuan & C.-C Liao (2009) *Actinomadura miaoliensis* sp. nov., a thermotolerant polyester-degrading actinomycete. *Int. J. of Systematic and Evolutionary Microbiology* 59, 517-520.

Nakajima, Y., Kitpreechavanich, V., Suzuki, K. & Kudo, T. (1999). Microbispora coralline sp. nov., a new species of the genus Microbispora isolated from That soil. *Int. J. System. Bacteriol.* 49, 1761-1767.

Sanchez, J. G., Tsuchii, A. & Tokiwa, Y. (2000). Degradation of polycaprolactone at 50° C. by a thermotolerant *Aspergillus* sp. Biotechnol. Lett. 22, 849-853.

Shirling, E. B. & Gottlieb, D. (1966). Methods for characterization of *Streptomyces* species. *Int J Syst Bacteriol* 16, 313-340.

Takeda, M., Koizumi, J., Yabe, K. & Adachi, K. (1998). Thermostable poly(3-hydroxybutyrate) depolymerase of a thermophilic strain of *Leptothrix* sp. isolated from a hot spring. *J. Ferment. Bioeng.* 85, 375-380.

Tamaoka, J. & Komagata, K. (1984). Determination of DNA base composition by reversed-phase high-performance liquid chromatography. *FEMS Microbiol Lett* 25, 125-128.

Tansengco, M. L. & Tokiwa, Y. (1998). Thermophilic microbial degradation of polyethylene succinate. *World J. Microbiol. Biotechnol.* 14, 133-138.

Thompson, J. D., Gibson, T. J., Plewniak, F., Jeanmougin, F. & Higgins, D. G. (1997). The Clustal X windows interface: flexible strategies for multiple sequence alignment aided by quality analysis tools. *Nucleic Acids Research* 24, 4876-4882.

Tokiwa, Y, & Pranamuda, H. (2001). Microbial degradation of aliphatic polyesters. In: Doi Y, Steinbuchel A eds. Biopolymers. Vol. 3. Weinheim: Wiley-VCH, pp. 85-103.

Tokiwa, Y., Iwamoto, A., Koyama, M., Kataoka, N. & Nishida, H. (1992). Biological recycling of plastics containing ester bonds. *Macromol. Chem. Macromol. Symp.* 57: 273-279.

Wayne, L. G., Brenner, D. J., Colwell, R. R. & 9 other authors (1987). International Committee on Systematic Bacteriology. Report of the ad noc committee on reconciliation of approaches to bacterial systematics. *Int. J. Syst. Bacteriol.* 37: 463-464.

---

The invention claimed is:

1. An isolated *Actinomadura* sp. capable of degrading a polyester, said *Actinomadura* sp. comprises:
   short spores chain on the tips of aerial mycelium;
   non-motile and rod spores with a spiny surface;
   blue aerial spore mass;
   an absence of soluble pigment production;
   an ability to grow at about 25° C. to 55° C.;
   an ability to hydrolyse casein, aesculin and L-tyrosine;
   an ability to produce nitrate reductase;
   an ability utilize glucose, xylose, rhamnose, sorbitol, fructose, trehalose and lactose; and
   a DNA-DNA hybridization rate with *Actinomadura miaoliensis* BC44T-5 of at least 70%, wherein *Actinomadura miaoliensis* BC44T-5 is deposited with the ATCC under the accession number PTA-8409.

2. The isolated *Actinomadura* sp. of claim 1, wherein the polyester is poly(D-3-hydroxybutyrate) (PHB).

3. The isolated *Actinomadura* sp. of claim 1, wherein the DNA-DNA hybridization rate is at least 75%, 80%, 90%, or 95%.

4. The isolated *Actinomadura* sp. of claim 1, which is *Actinomadura miaoliensis* BC44T-5 or an isolated variant or isolated mutant thereof having all the identifying characteristics of said *Actinomadura miaoliensis* BC44T-5.

5. A composition comprising the isolated *Actinomadura* sp. of claim 1.

6. A combination comprising the composition of claim 5 in combination with one or more other polymer-degrading microorganisms.

7. A composition comprising the isolated *Actinomadura* sp. of claim 4.

8. A method comprising providing a composition comprising the isolated *Actinomadura* sp. of claim 4 in combination with one or more other polymer-degrading microorganisms and contacting a polyester with the composition to degrade the polyester.

9. A method for degrading polyesters comprising the step of contacting a polyester with the isolated *Actinomadura* sp. of claim 1.

10. The method of claim 9, wherein the polyester is PHB.

11. A method for degrading polyesters comprising the step of contacting a polyester with the isolated *Actinomadura* sp. of claim 4.

12. The method of claim 11, wherein the polyester is PHB.

13. A method for degrading polyesters comprising the step of contacting a polyester with the composition of claim 5.

14. A method for degrading polyesters comprising the step of contacting a polyester with the composition of claim 6.

15. The method of claim 14, wherein the polyester is PHB.

16. A method for degrading polyesters comprising the step of contacting a polyester with the composition of claim 7.

17. The method of claim 16, wherein the polyester is PHB.

18. A method for degrading polyesters comprising the step of contacting a polyester with the composition of claim 8.

19. The method of claim 18, wherein the polyester is PHB.

* * * * *

UNITED STATES PATENT AND TRADEMARK OFFICE
CERTIFICATE OF CORRECTION

| | | |
|---|---|---|
| PATENT NO. | : 8,476,056 B2 | Page 1 of 1 |
| APPLICATION NO. | : 12/858492 | |
| DATED | : July 2, 2013 | |
| INVENTOR(S) | : Hoang et al. | |

It is certified that error appears in the above-identified patent and that said Letters Patent is hereby corrected as shown below:

On the title page, (item 73) the Assignee information should appear as follows:

(73)  Assignee:  Food Industry Research and Development Institute, Taiwan (R.O.C.)

Signed and Sealed this
Thirty-first Day of December, 2013

Margaret A. Focarino
*Commissioner for Patents of the United States Patent and Trademark Office*

SEQUENCE LISTING

```
<160> NUMBER OF SEQ ID NOS: 1

<210> SEQ ID NO 1
<211> LENGTH: 1514
<212> TYPE: DNA
<213> ORGANISM: Actinomadura sp.
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t

<400> SEQUENCE: 1
tagagtttga tcctggctca ggacgaacgc tggcggcgtg cttaacacat gcaagtcgag      60
cggaaaggcc ccttcggggg tactcgagcg gcgaacgggt gagtaacacg tgagcaacct     120
gcccctgact ctgggataag cctgggaaac cgggtctaat accggatacg acctccgtng     180
gcatccnttg gtggtggaaa gttttcggt tggggatggg ctcgcggcct atcagcttgt     240
tggtggggtg atggcctacc aaggcgacga cgggtaaccg gcctgagagg gcgaccggtc     300
acactgggac tgagacacgg cccagactcc tacgggaggc agcagtgggg aatattgcgc     360
aatgggcgga agcctgacgc agcgacgccg cgtggggat gacggccttc gggttgtaaa      420
cctctttcag cagggacgaa gctttcgggt gacggtacct gcagaagaag cgccggctaa     480
ctacgtgcca gcagccgcgg taatacgtag ggcgcaagcg ttgtccggaa ttattgggcg     540
taaagagctc gtaggtggtt tgtcgcgtcg gatgtgaaag cccatggctt aactgtgggt     600
ctgcattcga tacgggcaga ctagaggtag gtaggggagc atggaattcc cggtgtagcg     660
gtgaaatgcg cagatatcgg gaggaacacc ggtggcgaag gcggtgctct gggccttacc     720
tgacgctgag gagcgaaagc gtggggagcg aacaggatta gataccctgg tagtccacgc     780
cgtaaacgtt gggcgctagg tgtggggttc ttccacggat tccgcgccgt agctaacgca     840
ttaagcgccc cgcctgggga gtacggccgc aaggctaaaa ctcaaaggaa ttgacggggg     900
cccgcacaag cggcggagca tgttgcttaa ttcgacgcaa cgcgaagaac cttaccaagg     960
cttgacatca cccgaaaact cgcagagatg cggggtcctt tttgggcggg tgacaggtgg    1020
tgcatggctg tcgtcagctc gtgtcgtgag atgttgggtt aagtcccgca acgagcgcaa    1080
ccctcgttcc atgttgccag cacgtagtgg tggggactca tgggagaccg ccggggtcaa    1140
ctcggaggaa ggtggggatg acgtcaagtc atcatgcccc ttatgtcttg ggctgcaaac    1200
atgctacaat ggccggtaca gagggctgcg ataccgtgag gtgagcgaa tcccttaaag    1260 ccggtctcag ttcggattgg ggtctgcaac tcgaccccat gaagtcggag tcgctagtaa    1320
```

```
tcgcagatca gcaacgctgc ggtgaatacg ttcccgggcc ttgtacacac cgcccgtcac    1380
gtcacgaaag tcggcaacac ccgaagcccg tggcccaacc ctttgggggg gagcggtcga    1440
aggtggggcc ggcgattggg acgaagtcgt aacaaggtag ccgtaccgga aggtgcggct    1500
ggatcacctc ctta                                                     1514
```